US005712310A

United States Patent [19]

Koch

[11] Patent Number: 5,712,310
[45] Date of Patent: Jan. 27, 1998

[54] SUSPENSION OF SUBSTANTIALLY WATER-INSOLUBLE DRUGS AND METHODS OF THEIR MANUFACTURE

[75] Inventor: Edward A. Koch, New Freedom, Pa.

[73] Assignee: Alpharma USPD, Inc., Baltimore, Md.

[21] Appl. No.: 664,338

[22] Filed: Jun. 14, 1996

[51] Int. Cl.$^6$ .......................... A61K 9/107; A61K 31/19
[52] U.S. Cl. ..................................................... 514/570
[58] Field of Search ............................................. 514/570

[56] References Cited

U.S. PATENT DOCUMENTS

| | | | |
|---|---|---|---|
| 4,282,215 | 8/1981 | Dudzinski et al. | 514/161 |
| 4,404,210 | 9/1983 | Schmidt | 514/282 |
| 4,569,937 | 2/1986 | Baker et al. | 514/282 |
| 4,571,400 | 2/1986 | Arnold | 514/282 |
| 4,587,252 | 5/1986 | Arnold | 514/282 |
| 4,783,465 | 11/1988 | Sunshine et al. | 514/255 |
| 4,788,220 | 11/1988 | Mody et al. | 514/557 |
| 4,857,331 | 8/1989 | Shaw et al. | 424/440 |
| 4,859,704 | 8/1989 | Haas | 514/557 |
| 5,183,829 | 2/1993 | Caldwell | 514/570 |
| 5,374,659 | 12/1994 | Gowan, Jr. | 514/557 |
| 5,401,510 | 3/1995 | Robertson et al. | 424/427 |

FOREIGN PATENT DOCUMENTS

WO 92/00731  1/1992  WIPO.

OTHER PUBLICATIONS

Technical Bulletin DB-33 *Xanthan Gums For Food and Pharmaceutical Applications*, Kelco a Division of Merck & Co., Inc. 1–3.

S.L. Law et al. *Drug Development and Industrial Pharmacy*, 10(7), 1049–1069 (1984).

*Primary Examiner*—Alan L. Rotman
*Assistant Examiner*—D. Margaret M. Mach
*Attorney, Agent, or Firm*—Lerner, David, Littenberg, Krumholz & Mentlik

[57] ABSTRACT

A stable aqueous suspension including a substantially water-insoluble drug suspended in a completely water-soluble mixture including hydroxypropylmethylcellulose, polyoxyethylene sorbitan monooleate, and xanthan gum.

56 Claims, 1 Drawing Sheet

SUSPENSION OF SUBSTANTIALLY WATER-INSOLUBLE DRUGS AND METHODS OF THEIR MANUFACTURE

FIELD OF THE INVENTION

The present invention relates to the pharmaceutical field and, in particular, to the design of drug suspensions for substantially water-insoluble drugs, such as ibuprofen, and methods of manufacturing same.

BACKGROUND OF THE INVENTION

Few drugs since the introduction of aspirin have had as pronounced an effect on the pharmaceutical industry and the consuming public as ibuprofen. Since the FDA approved the sale of ibuprofen as an over-the-counter drug, its popularity has climbed dramatically. Today, ibuprofen is one of the most recognized and most used drugs for aches, pains, and fevers.

Nonetheless, ibuprofen, like many other substantially water-insoluble drugs, has been unable to fulfill its full potential in the marketplace, particularly in areas where liquid dosage forms are preferred. Children, older persons, and many others, including disabled and incapacitated patients, have trouble swallowing whole tablets or even capsules. Drug suspensions, properly formulated, could find ready acceptance with these very important groups of patients. Not surprisingly, there have been numerous attempts to formulate aqueous pharmaceutical suspensions of substantially water-insoluble pharmaceutical active ingredients, such as, for example, ibuprofen. Many of these formulations, while satisfactory, still leave room for improvement.

For example, numerous drugs have been formulated in solutions and suspensions with alcohol (ethanol). However, such formulations are obviously unsuitable for children, alcoholics and those on certain drugs. Gowan, Jr., U.S. Pat. No. 5,374,659, teaches an aqueous pharmaceutical suspension including a water-insoluble active ingredient such as ibuprofen, in a suspension comprised of xanthan gum, pregelatinized starch, and polyoxyethylene sorbitan monooleate (polysorbate 80), a taste-masking composition, and water. However, while Gowan's formulation excludes ethanol, it is not without its problems.

First, one of Gowan's disclosed ingredients is a corn starch. Corn starch is a known allergen. Thus the Gowan formulation would be contraindicated in those people, particularly children, with a known corn allergy. Furthermore, corn starch supports microbial growth and is subject to microbial degradation. While Gowan does disclose the use of an antimicrobial agent, the starch is added prior to the addition of the antimicrobial agent. Thus there is an increased potential for microbial growth during the manufacturing process. Microbial growth during manufacturing places a greater burden on the antimicrobial agent and could lead to chemical and physical changes in the corn starch itself. This could affect the properties of formulations from batch to batch.

It is therefore desirable to produce a suspension which excludes starch. One possible candidate to replace starch is microcrystalline cellulose. In fact, such a formulation is discussed in Mody et al. U.S. Pat. No. 4,788,220. Though the use of microcrystalline cellulose will overcome some of the disadvantages of corn starch, it is, nonetheless, a water-insoluble material. Therefore, it is not without its own limitations.

As to solubility, insoluble materials such as starch, microcrystalline cellulose or clays such as magnesium aluminum silicate, which are often used as suspending agents, may mask inhomogeneity in the product. Thus, while a product may look homogeneous, the active ingredient is not evenly distributed throughout the suspension. A consumer might then ignore instructions to shake before using because the product appears visibly homogeneous. Under such circumstances, if the drug was not, in fact, homogeneously dispersed, the patient could potentially receive either a sub-potent or super-potent dose.

Another disadvantage which stems from the use of insoluble materials (other than the drug substance) in a drug product suspension is that the drug substance particle size in the dosage form is more difficult to evaluate. The drug particle size in a suspension can affect the bioavailability and the physical stability of the dosage form. Thus monitoring the drug particle size, both at the time of manufacture and during shelf storage, is an important parameter from both a quality and regulatory standpoint. One of the most common techniques is the use of a laser light scattering instrument such as manufactured by Malvern or Coulter. These instruments are able to take a large number of replicate readings in a short period of time with a relatively large sample size as compared to the alternate manual sizing using a microscope. However, laser light scattering instruments cannot differentiate between the insoluble drug particles and the insoluble suspending agents making all such measurements imprecise. The alternative to laser light scattering would be direct manual microscopic particle sizing. This technique is costly in terms of the analysis time and it is more subjective, thus less precise. Other formulations have also been proposed such as those described in Caldwell, U.S. Pat. No. 5,183,829.

SUMMARY OF THE INVENTION

The inventor has created a new, water-soluble, suspension vehicle which is useful for the administration of generally water-insoluble drugs such as ibuprofen and which overcomes the shortcomings identified in the prior art. In a preferred aspect, the present invention provides a storage stable, aqueous suspension for delivery of at least one substantially water-insoluble pharmaceutically active agent. The suspension includes at least one substantially water-insoluble pharmaceutically active agent provided in an amount which is effective to treat a patient in need of such treatment. The substantially water-insoluble pharmaceutically active agent is suspended in a formulation which includes a first suspending agent which is a pharmaceutically acceptable, non-ionic, water-soluble, modified cellulose. The formulation also includes a second suspending agent which is a water-soluble, hydrocolloidal polysaccharide. The suspension also includes a non-ionic, water-soluble wetting-agent. The first suspending agent, the second suspending agent and the wetting-agent are provided in amounts which are effective to form a stable suspension of the water-insoluble pharmaceutically active agent.

In a particularly preferred aspect of the present invention, the substantially water-insoluble pharmaceutically active agent is selected from a group consisting of cardiovascular drugs, hypoglycemic drugs, sedatives/hypnotics, antiepileptics, psycholpharmacologic agents, analgesics, antipyretics, anti-inflammatory agents, anti-neoplastics and antimicrobials. Most preferably, the modified cellulose is hydroxypropyl methylcellulose. The second suspending agent preferably has a shear thinning profile similar to that of xanthan gum. That is to say that the second suspending agent is capable of imparting, in combination with these formulations, a suspension exhibiting at least a 100% increase in viscosity for each log decrease of shear rate in the range of 20 sec$^{-1}$ to 0.2 sec$^{-1}$. Most preferably, the second suspending agent is xanthan gum. The wetting-agent is preferably polysorbate 80.

It is advantageous for the suspensions of the present invention to also include at least one additional material selected from a group consisting of a sweetener, a humectant, a viscosity modifier, an antimicrobial agent, a pH modifier, a flavoring and/or a coloring.

In another preferred aspect of the present invention, there is provided a storage stable, aqueous suspension for delivery of at least one substantially water-insoluble pharmaceutically active agent. The suspension includes at least one substantially water-insoluble pharmaceutically active agent selected from a group consisting of: analgesics, antipyretics, and anti-inflammatory agents. The substantially water-insoluble pharmaceutically active agent can be present in an mount of between about 0.1% and about 20% w/v. The pharmaceutically active agent is suspended in a formulation including a first suspending agent which is a pharmaceutically acceptable, non-ionic, water-soluble, modified cellulose provided in an amount of between about 0.4% and about 1% w/v, a second suspending agent which is a water-soluble, hydrocolloidal polysaccharide being provided in amount of between about 0.1% and about 1.0% w/v and a water-soluble, non-ionic wetting-agent provided in an amount of between about 0.025% and about 0.4% w/v.

Most preferably, the present invention provides a stabilized suspension comprising ibuprofen in amounts between about 0.5% and about 8 w/v, hydroxypropyl methylcellulose in an amount of between about 0.4% and about 1% w/v, xanthan gum provided in an amount of between about 0.1% and about 1.0% w/v, polyoxyethylene sorbitan monooleate in an amount of between about 0.025% and about 0.4% w/v, sucrose in an amount of between about 20% and about 40% w/v, glycerin in an amount of between about 1% and about 40% w/v, an antimicrobial agent in an amount of between about 0.05% and about 0.5% w/v; a pH modifier in an amount of between about 0.05% and about 1.0% w/v, at least one flavoring and water.

Stated another way, in one aspect of the present inventions there is provided a suspension which is composed exclusively of generally water-soluble ingredients, other than the pharmaceutically active agent. That suspension is stable, non-reactive, cost effective, and overcomes many of the disadvantages that are inherent in suspensions created using substantially water insoluble ingredients. The aqueous suspension formulations of the present invention could be used in many contexts. But they are particularly useful as drug delivery vehicles. In fact, it has been found that the suspensions of the present invention, made of generally water soluble components, are an excellent means for suspending otherwise substantially water-insoluble pharmaceutically active agents or drugs.

Suspensions of substantially water-insoluble drags suspended in the formulations of the present invention have several advantages over the prior art. First, because the present invention eliminates corn starch, the resulting dosage form can be administered to patients with corn starch allergies. Further, the elimination of starch from the formulation reduces the risk of bacterial growth during processing as well as the viability in the formulation that may result. Moreover, because the present invention does not generally use substantially water-insoluble materials, other than the drug, better process control is possible. The potential for masking of an inhomogeneous dispersion of the drug is also eliminated.

DETAILED DESCRIPTION OF PREFERRED EMBODIMENTS

A suspension in accordance with the present invention must satisfy several criteria. First, it must be a suspension as opposed to a slurry, emulsion, solution or gel. A pharmaceutical suspension can generally be defined as a coarse dispersion in which insoluble solid particles are dispersed in a liquid medium. The particles have diameters, for the most part, greater than about 0.1 micrometers, and some of the particles are observed under the microscope to exhibit Brownian movement if the dispersion has a low viscosity. Suspensions can be flocculated or structured. Structured suspensions are preferred, however, some flocculation in a structured suspension is possible under certain conditions. In addition, the suspensions must be stable, both in terms of the nonreactivity of the various components and in terms of long term storage stability. A "stable" suspension in accordance with the present invention is one which can be redispersed homogeneously with moderate shaking and can be poured easily throughout its shelf life, with neither the particle size distribution, the form or the physiological availability of the suspended active agent changing appreciably with time. The stability of a suspension is often judged by criteria set in the U.S.P. listed under the heading "Stability Considerations in Dispensing Practice." These criteria require, inter alia, that the original physical properties, including appearance, palatability, uniformity, dissolution and suspendability of the suspension be retained. Most preferably, a suspension in accordance with the present invention will have a viscosity profile which will vary with the conditions applied to the suspension. For example, preferably, a bottle containing a suspension of the present invention will exhibit a generally low viscosity when the bottle is shaken or when the bottle is manipulated during pouring. However, when the suspension is sedentary, its relative viscosity will increase to assist in maintaining the integrity of the suspension and the homogeneous distribution of the active ingredient(s).

The suspension should also be cost-effective to manufacture and should reduce the concerns any patient may have with regards to adverse reactions to its ingredients. Finally, in accordance with the present invention, the suspension should be a substantially aqueous dosage form which can be effectively used for the administration of water-insoluble or sparingly water-soluble drugs.

For the purposes of the present invention, the terms "substantially water-insoluble" and "insoluble" refer generally to compositions which are insoluble, practically insoluble or only slightly soluble in water as those terms were defined in the U.S.P., Remington: "Pharmaceutical Science", 18th edition published by Mack Publishing Company and as used in the industry. Substantially water-insoluble pharmaceutically active ingredients include, for example, cardiovascular drugs, e.g. cardiac glycosides, clofibrate and probucol; hypoglycemic drugs; sedatives/hypnotics, e.g. barbiturates; and antiepileptics, e.g. carbamazepine, mephenytoin and phenytoin; psycholpharmacologic agents e.g. perphenazine, analgesic antipyretic and anti-inflammatory agents, e.g. naproxen, oxycodone and indomethacin; anti-neoplastic drugs such as almitrine; and antimicrobials such as erythromycin estolate. In accordance with the present invention, particularly preferred classes of insoluble drugs include: analgesics, antipyretics, anti-inflammatory agent, antimicrobials, decongestants and antihistamines. Ibuprofen suspensions are particularly preferred in accordance with the present invention.

In general, aqueous pharmaceutical suspensions in accordance with the present invention will include an amount of at least one water-insoluble, pharmaceutically active agent which is sufficient to treat a patient in need of treatment with that active drug. Of course, the amount of active agent used will vary with the size, sex, age, general health and condition of the patient and the type of drug and suspension. However, generally, from about 0.1% to about 20% weight to volume ("w/v") of at least one substantial water-insoluble pharmaceutical active agent is used. Of course, it is possible, depending on the nature of the dosage form, the drug(s), and the indication(s), to create suspensions in accordance with the present invention that have greater than about 20% and/or less than about 0.5% of at least one insoluble active ingredient.

More preferably, however, on a weight to volume basis, the amount of the substantially water-insoluble pharmaceutically active agent included in the suspensions of the present invention ranges from between 0.5% to about 10%. In terms of ibuprofen, the suspension preferably contains between 0.5% to about 8% ibuprofen w/v. More preferably, the suspensions in accordance with the present invention contain between 1% and about 4% active (such as ibuprofen) and most preferably about 2% w/v. The particles should have an median diameter of at least about 0.1 micrometers. The maximum particle size is not critical so long as the particles are capable of being maintained in a stable suspension. However, particle sizes of up to about 100 microns (median diameter) and preferably up to about 50 microns are useful in accordance with the present invention. Particles in a size range of between about 15 and about 35 microns are particularly preferred.

The suspensions in accordance with the present invention are principally achieved by combining the drug with three ingredients including a first water-soluble suspending agent, a second water-soluble suspending agent and a water-soluble surfactant. The balance, of course, is water.

In accordance with the present invention, the first water-soluble suspending agent can be any pharmaceutically acceptable, non-ionic, water-soluble, modified cellulose. Particularly preferred modified cellulose compounds include hydroxypropyl cellulose ("HPC"), methyl cellulose ("MC"), hydroxyethylcellulose ("HEC") and hydroxypropyl methylcellulose ("HPMC").

It has been found that such water-soluble suspending agents may be used in place of such compounds as starch and microcrystalline cellulose, thereby overcoming the problems associated with insoluble suspending agents. In view of the arts' use of insoluble suspending agents, it was surprising to learn that using water-soluble suspending agents produced suspensions of equal or greater performance. It was even more surprising to find that only certain types of water-soluble suspending agents would work as the first suspending agent. Other conventional water-soluble suspending agents, such as, for example, guar gum, were found by the inventor to be inadequate first suspending agents. The use of the first water-soluble suspending agent described in accordance with the present invention eliminates the problems associated with the use of water-insoluble suspending agents, and in addition, eliminates one potential source of an allergic response and microbial growth from the formulation.

It has also been discovered that in addition to the general advantages which inure from the use of certain water-soluble suspending agents as described herein, certain specific water-soluble suspending agents, such as HPMC, provide unexpected and superior results. For example, it was previously reported by Law and Kayes, "The Stability Of Suspensions In The Presence Of Non-Ionic Water-soluble Cellulose Polymers," *Drug Development and Industrial Pharmacy*, 10(7), 1049–1069 (1984), that an ibuprofen suspension could be made using HPMC. The authors reported that at low levels of HPMC, (0.04%) a re-dispersible dispersion of flocs could be formed. However, as the concentration of HPMC exceeded 0.04%, caking resulted which led to high redispersibility values (meaning it was difficult to form a homogeneous suspension). The authors went on to state that at higher polymer levels, a gel structure could result which would lead to increased difficulty in obtaining a homogeneous dispersion. In fact, the Law and Kayes article specifically speaks of forming a flocculated suspension using low level (0.04% and lower) of HPMC. When levels were increased to 0.08%, the suspensions were deflocculated and formed a cake which was difficult to re-disperse.

It has been found, however, that using the system of the present invention, it is possible to use HPMC at levels which are as much as 1000% higher than that suggested by Laws and Kayes, while at the same time, obtaining stable suspensions which are neither visibly flocculated nor caked. In accordance with the present invention, flocculation occurs at around 0.3% HPMC. By increasing the concentration of HPMC to at least about 0.4% and more preferably at about 0.6%, visible flocculation was eliminated and a structured suspension was produced which showed neither separation nor caking. Of course, the occurrence of floc in a suspension is less desirable than a fully structured, homogeneous suspension. However, as flocs can be readily re-dispersed within a suspension upon shaking, it is far more desirable to obtain flocculation than to obtain a non-redispersable cake. For that reason, the first water-soluble suspending agent can be used in an amount of as little as about 0.2%. However, preferably between about 0.4% and about 1% and more preferably between about 0.5% and about 0.7% w/v of HPMC is used. Most preferably, HPMC is provided as a first suspending agent in an amount of about 0.6% w/v. The preferred ranges also apply generally to any first water-soluble suspending agent used in accordance herewith. HPMC is Available from Dow Chemical Co., Midland Mich. 48674.

Figure 1:
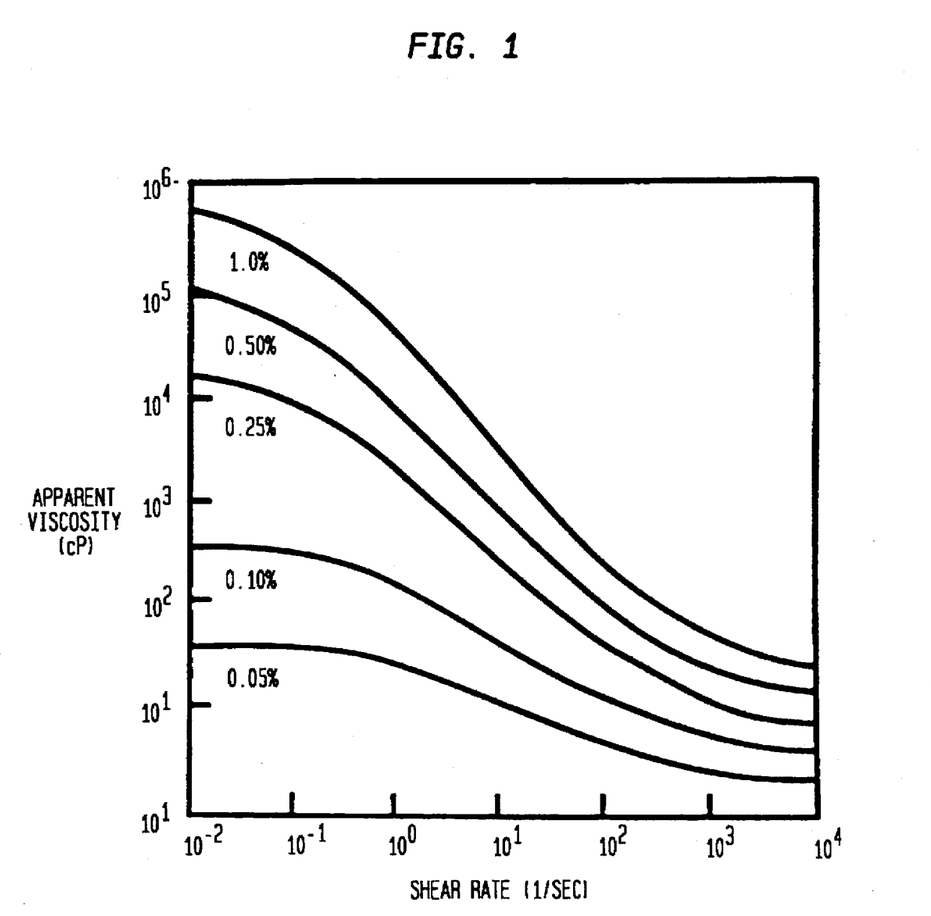
FIG. 1. illustrates the relationship between viscosity and shear rate for solutions containing KELTROL T brand Xanthan Gum available from Kelko, a division of Merck & Co., Inc., over a shear rate range between 0.01 and 10,000 1/sec as measured on the Rheometrics Fluids Rheometer.

The second principal ingredient of the suspension is the second water-soluble suspending agent. This second suspending agent is intended to provide the suspension with a specific viscosity profile. Generally, the second suspending agent is a water-soluble hydrocolloidal polysaccharide such as guar gum, carrageenan gum, gum arabic and xanthan gum. Certain materials, such as for example, xanthan gum have known viscosity profiles which vary responsive to an applied shear. This is also referred to as a "shear thinning profile." For example, KELTROL T, a xanthan gum available from Kelko, a division of Merck & Co., Inc. 75 Terminal Ave. Clark, N.J. 07066, exhibits an increase in apparent viscosity with a decrease in applied shear. The viscosity or shear thinning profile for xanthan gum and other similar compounds are well known and well documented. See FIG. 1. Any material which can provide a similar shear thinning profile to xanthan gum could be used for in accordance with the present invention. Stated another way, compounds useful as the second suspending agent in accordance with the present invention will have a shear thinning profile whereby a suspension exhibiting at least a 100% increase in viscosity for each log decrease of shear rate in the range of 20 sec$^{-1}$ to 0.2 sec$^{-1}$ results. In fact, for a log decrease in shear from 20 sec$^{-1}$ to 2.0 sec$^{-1}$, the viscosity of the suspension should double. From 2.0 sec$^{-1}$ to 0.2 sec$^{-1}$, the viscosity of the suspension should about double again.

It should be noted that while such compounds as guar gum are unacceptable as the first suspending agent in accordance with the present invention, they are acceptable for use as the second suspending agent. The fact that the first and second suspending agents are not interchangeable is not important or surprising. What is important is that the two distinct suspending agents have two distinct functions in these formulations.

The second suspending agent must be included in an amount which is effective to provide the resulting suspension with the desired shear thinning profile. Generally, the amount of the second suspending agent used will vary depending upon the nature and quantity of the other ingredients as well as the second suspending agent selected. However, a range of between about 0.1% and about 1.0% w/v is generally useful. A more preferred range for the second suspending agent in accordance with the present invention is from between about 0.1% and about 0.3% w/v. Even more preferably, the amount of the second suspending agent used will range from between about 0.15% and about 0.21%. Xanthan gum is the preferred second suspending agent in accordance with the present invention, and when used, it is preferably used in an amount of about 0.18% w/v.

The non-ionic, water-soluble wetting-agent is the third necessary component. Such wetting-agents or surfactants are well known in the art and include, for example, polyoxyethylene sorbitan fatty acid esters, such as polyoxyethylene sorbitan monooleate also known as polysorbate 80. Other useful wetting-agents in accordance with the present invention include polyoxyethylene-polyoxypropylene copolymers which are poloxamers. Poloxamers such as poloxamer 124, 188, 237, 388 and 407 available from BASF Corp. of Parsippany, N.J. 07054 may also be used. Polyvinyl alcohol available from Spectrum Chemical Mfg. Corp., New Brunswick, N.J. 08901 may also be used as well.

The wetting-agent is generally provided in an amount of between 0.025% to about 0.4%, more preferably in the amount of 0.05% to about 0.2% and most preferably in amounts of about 0.1% weight to volume. The preferred wetting-agent in accordance with the present invention is polysorbate 80.

Water and preferably distilled, deionized water is the last necessary ingredient. Water is added as needed to dissolve the various components and to bring the suspensions to correct volume.

In addition to the principal ingredients just described, suspensions in accordance with the present invention also desirably contain a number of secondary ingredients including, without limitation, sweeteners, humectants, viscosity modifiers, antimicrobial agents, and pH modifiers. These ingredients may be included to the extent that they do not alter the basic and novel characteristics of the invention. Thus, these additives should be selected such that they will not unduly undermine the stability or other advantageous properties of the suspension. It has been found that certain secondary ingredients can actually enhance the stability, the viscosity and/or the organoleptic properties of these formulations. Obviously, the selection of such sweeteners, humectants, viscosity modifiers, antimicrobial agents and pH modifiers is preferred.

Without wishing to be bound by any particular theory of operation, sweeteners such as sucrose and humectants such as glycerin, at the concentrations used, contribute directly to the viscosity, stability and/or organoleptic properties of the suspension in that they are at least slightly more viscous than water. Second, these compounds also exhibit a direct effect on the formulations by reducing the total water quantity available, thereby increasing the effective concentrations of the suspending agents and wetting-agents. The other secondary ingredients will also have an affect on the viscosity, stability and organoleptic properties of the suspensions of the present invention. Antimicrobial agents such as, for example, sodium benzoate, and pH modifiers, such as citric acid, effect the ionic strength and the pH of the suspensions. Therefore, while only certain compounds will be discussed herein, it is understood that any functionally similar ingredient(s) could be used in their place.

Sweeteners in accordance with the present invention directly enhance the organoleptic properties of the suspensions and act as, inter alia, taste masking agents. As previously discussed, they also play a role in the viscosity and stability of the formulations. The preferred sweetener in accordance with the present invention is sucrose and, more preferably sucrose syrup #2 (67.4% w/w solution of sucrose in water) is used. Other acceptable sweeteners include, without limitation, sugars such as fructose and glucose and sweet polyhydric alcohols which are commonly used as sweeteners such as sorbitol, mannitol or xylitol. These sweeteners are all sweet, relatively non-ionic, and substantially water-soluble. The amount of sweetener used in accordance with the present invention can vary based on a number of factors. Of course, as the sweetener may have an effect on the viscosity of the suspension, sufficient sweetener must be provided so as to assist in providing the desired viscosity. Because the sweetener also plays a large role in taste masking, if the active agent is particularly bad tasting then more sweetener may be needed. Generally, the amount of sweetener ranges from between about 20% and about 40% w/v. However, preferably, the amount used should range between about 25% and about 35% w/v.

Another ingredient which should be used in the suspension of the present invention, particularly those which use a sugar as the sweetener, is a humectant. A humectant in accordance with the present invention preserves moisture, particularly around the threaded mouth of the bottle and the cap, to ensure that the sugar contained within the formulation does not crystallize, rendering it difficult to open the bottle. A particularly useful compound in accordance with this aspect of the invention is glycerin. Glycerin acts not only as a humectant, but, as previously discussed, also acts as a viscosity modifier in that it ties up water and has a viscosity that is greater than that of water. Moreover, glycerin is substantially non-ionic and water-soluble. It is also a sweetener and has antimicrobial efficacy. Other pharmaceutically acceptable humectants include, without limitation, propylene glycol and sorbitol. These humectants, as well as other known compounds, may also be used solely as viscosity modifiers for the suspensions of the present invention. For example, if sorbitol is used as the sweetener, then there is no reason to use a humectant. However, it may be desirable to add a viscosity modifier such as propylene glycol or glycerin to the sorbitol in an amount which is necessary to bring the viscosity of the suspension up to the desired level. The amount of the viscosity modifier/ humectant used can vary widely. However, a combined total of these compounds should generally range from between about 1% and about 40%, and more preferably between about 1% and about 15% w/v.

It should be noted that, although glycerin is sweet, it generally cannot be used as a complete substitute for sweeteners such as sucrose. First, glycerin does not have the sweetening power of sucrose. Thus a relatively high glycerin content would be needed. Moreover, glycerin, like propylene glycol, acts as a solvent which is a negative factor in accordance herewith. As more drug is solubilized, the potential for Otswald ripening increases thus increasing the potential for a change in the distribution of the drug from unimodal to multimodal. Changes in the size distribution of the drug particles, sedimentation rates and or changes in bioavailability may also result. Thus the selection and use of compounds in this system may often require a balance of factors.

Antimicrobial agents, such as sodium benzoate, potassium sorbate and sodium proprionate, to name but a few should also be used. These antimicrobial agents are well known in the industry. The antimicrobial agents used should not interfere with the suspension, must be water-soluble, and must not adversely affect the taste or the pH of the mixture. The amounts of such antimicrobial agents can vary widely. For example, the amount of sodium benzoate which may be used at a range of between about 0.05% and about 0.5% w/v. Preferably, the amount of antimicrobial agent used may range from between about 0.1% and about 0.5% w/v. However, the addition of, for example, too much sodium benzoate, may elevate the pH to a degree which will require the addition of an undesirable excess of a pH modifier.

The pH modifiers used in accordance with the present invention may be any food grade or pharmaceutical grade acid or base which is capable of maintaining the pH of the resulting formulation in a range of between about 2.5 and about 5.0. Preferably, the pH of the formulation is between about 3.6 and about 4.6. Citric acid is a preferred acidifying agent. Generally, the citric acid is provided in an amount of between about 0.05% and about 1.0% w/v. Any combination of antimicrobial agents and pH modifiers with yield a generally equivalent ionic strength and pH, and which are pharmaceutically acceptable, are contemplated.

Furthermore, to achieve the desired levels of ionic strength and pH, a weak acid and a salt of a week acid can be used. For example, the functions of an antimicrobial agent and a pH modifier can be obtained by the use of, for example a mixture of benzoic acid and sodium citrate.

While not in any way important to the formation of a stable suspension in accordance with the present invention, nonetheless, an acceptable combination of colorants, additional sweeteners and flavors are necessary to ensure that the resulting suspension has desirable organoleptic properties. Any conventional excipients can be used so long as they do not adversely affect the suspension and are water-soluble. Flavors can include vanilla, strawberry, cherry, mixed berry, raspberry, blackberry, banana, apple, pear, peach, grape, pineapple, mint, wintergreen, peppermint, spearmint, cinnamon, spice, chocolate, hazelnut, coffee and the like. Dyes acceptable for orally ingested products which are detailed in the Code of Federal Regulations may also be used.

The resulting suspensions preferably have a viscosity of about 100 centipoise when measured at a temperature of about 25° C. and at a shear rate of 20 sec$^{-1}$. As previously mentioned, the viscosity should at least about double for each log decrease in the shear rate. There is no real upper limit to the viscosity of the suspensions so long as they remain free flowing and pourable liquids. However, after shaking, the suspension should be easily dispensed by the consumer.

Thus the suspensions of the invention can be considered as consisting essentially of a first water-soluble suspending agent, a second water-soluble suspending agent having a specific viscosity profile, a water-soluble wetting-agent and water. Other ingredients can also be added so long as they do not detract from the advantageous properties of the suspensions of the present invention. These may include, without limitation, sweeteners, humectants, viscosity modifiers, antimicrobial agents and pH modifiers, as well as flavorings, coloring and other conventional excipients. Ingredients which actually enhance the properties of the suspensions, such as sucrose, glycerin, sodium benzoate and citric acid, and their functional equivalents, are specifically contemplated hereby.

In particularly preferred aspects of the present invention, the suspensions are formulated without the use of generally water-insoluble compounds or components. Of course, relatively small amounts of such compounds, or insoluble compounds that may be very small in terms of particle size, may be used, so long as they neither compromise the utility of the suspension nor significantly detract from the advantages which result from the use of water soluble ingredients.

The suspensions of the invention can generally be made by any conventional process. This includes the use of the sequential addition of various components to a main phase. Specifically, a slurry is created by the addition of hot (80°–85° C.) purified water USP (deionized water) and the HPMC in a mixing vessel. The HPMC is mixed in the hot water until a uniform slurry is produced. Thereafter, cold water is added to the mixing vessel. The cold water should be about room temperature or below. Agitation continues during this second water addition such that a uniform slurry is maintained. Thereafter, the resulting mixture is force cooled to below 25° C. This can be accomplished by, for example, using a jacketed vessel with suitable coolant. It is possible to refrigerate the main phase created hereby to any temperature above freezing. However, a temperature of greater than 5° C. and below about 25° C. is preferred.

In a separate vessel, a small portion (approximately 10%) of glycerin USP (96%) is charged and the xanthan gum is then dispersed therein. This is accomplished again using constant mixing. The remaining 90% or so of the glycerin is added to the force-cooled main phase, also with constant mixing, such that a homogeneous solution is formed. Upon completion of the dispersion of the glycerin and xanthan gum, mixing is stopped and the resulting slurry is immediately added to the main phase. Mixing of the main phase continues.

A further quantity of purified water at a temperature of between 50° to about 55° C. is then transferred to a separate mixing container and the surfactant is added thereto. The antimicrobial agent is then dissolved in the solution, again with constant mixing. The resulting solution of antimicrobial agent, surfactant and water is then added to the main phase while mixing continues.

After the addition of the wetting-agent-containing solution, an acidifying agent is used to adjust the pH of the main phase, where necessary, to between about 2.5 to about 5 and more preferably from between a pH of 3.6 and about 4.6. A sweetener is then added and dissolved in the main phase while mixing. Thereafter, the insoluble drug is then dispersed into the main phase while mixing.

Warm water (40°–45° C.) is then charged to a separate mixing vessel to which is added the necessary coloring agents. Generally, enough warm purified water is added so as to completely dissolve all of the coloring agents used. Thereafter, the dye solution is added the main phase while mixing continues. Finally, a solution is produced of the flavoring ingredient(s). The flavor solution is then added to the main phase while mixing continues.

After all the ingredients have been added to the formulation, the batch weight is then adjusted with purified water to arrive to the theoretical final weight. Preferably, the batch is then passed through a colloid mill. Finally the batch will be deaerated.

EXAMPLES

Example 1

Two formulations in accordance with the present invention were prepared as follows:

TABLE A

| Ingredient | Formula A Amount | Formula B Amount |
|---|---|---|
| HPMC | 6.00 g | 7.80 g |
| Glycerin USP (96%) | 80 ml | 80 ml |
| Xanthan Gum, NF | 1.80 g | 2.34 g |
| Polysorbate 80, NF | 1 g | 1 g |
| Sodium Benzoate, NF | 2 g | 2 g |
| Citric Acid, USP anhydrous | 2 g | 2 g |
| Sucrose Syrup #2 | 333 ml | 333 ml |
| Ibuprofen USP | 20 g | 20 g |
| FD&C Red #40 | 0.0100 g | 0.0100 g |
| D&C Yellow #10 | 0.0250 g | 0.0250 g |
| Flavors | 0.6 g | 0.6 g |
| Deionized Water Q.S.A.D. (balance) | 1000 ml | 1000 ml |

*All materials recited in quantity (weight to volume) per liter.

200 ml hot (80°–85° C.) deionized water was added to a suitable beaker. The HPMC was next added to the deionized water and mixed for 15 minutes using a lighting mixer. Next, 347 ml of ambient temperature (room temperature—approximately 25° C.) deionized water was added to the mixture while mixing was continued. The mixture was then cooled to a temperature below 25° C. while mixing continued. This now constitutes the main phase.

10 ml of glycerin was charged to a separate container and the xanthan gum was added thereto. At the same time, the remaining glycerin was added to the main phase and mixed. The mixed xanthan gum/glycerin slurry was then added to the main phase and mixed for 1½ hours.

In a separate beaker, 9.5 ml of water at a temperature of about 45° C. and about 50° C. was charged. The polysorbate 80 and sodium benzoate were then added to the warm water and mixed for 15 minutes using a magnetic stirrer at moderate speed. The mixture was then added to the main phase while mixing continued. Then, the citric acid was added to the main phase while mixing continued for approximately 10 minutes at the same speed.

The sucrose syrup was next added to the main phase. After the addition thereof, the speed of the mixer was increased for a period of 20 minutes. Next, the ibuprofen was added to the main phase. The main phase was then mixed for 3 hours.

In a separate container, 1 ml of deionized water at a temperature of between 35° C. and about 45° C. was added and the red and yellow dyes were added thereto. This mixture was mixed for 10 minutes by magnetic stirrer and then added to the main phase. A solution was made of the flavors as well. This solution was then added to the main phase and mixing continued for 20 additional minutes. Finally, the batch was adjusted to a theoretical yield by the addition of deionized water and mixing continued for 20 minutes. Formula A was milled and dearated. Formula B was not dearated. In each instance, mixing was sufficient to insure a good agitation of the batch without incorporating air.

The resulting materials were stable, opaque orange in color, and judged acceptable in terms of homogeneity, viscosity profile and organoleptic qualities. Furthermore, using standard validated analytical procedures, the resulting formulations showed acceptable storage stability for greater than three months.

Example 2

A suspension was produced as described in Example 1 except that the first suspending agent used was 0.6% w/v of methylcellulose was used in place of HPMC. Processing was identical except that the batch was force cooled to below 8° C. The lower temperature was necessary to fully hydrate the methycellulose.

The resulting material was stable, opaque orange in color, and judged acceptable in terms of homogeneity, viscosity profile and organoleptic qualities.

Example 3

A suspension was produced as described in Example 1 except that the first suspending agent used was 0.6% w/v of HEC was used in place of HPMC. Further, since the HEC does not need to be hydrated in the same fashion as HPMC, the beginning of the protocol was slightly changed. The HEC was dissolved in warm (50°–55° C.) deionized water. There was no need to force cool the HEC as it hydrates in warm water. From this point on, the protocols are identical, but the temperature of the batch was slightly higher since force cooling was not necessary.

Example 4

A suspension was produced as generally described in Example 1 except that the first suspending agent used was 0.5% w/v of gum arabic (5.00 g/1 L) was used in place of HPMC and the level of Xanthan gum was increased to 0.2% w/v (2.00 g/1 L). The general protocol described in Example 1 was also modified as follows. First, the xanthan gum was dispersed in all of the glycerin. This dispersion was then added to 400 ml of Deionized water and mixed for 30 minutes to form the main phase. Second, the gum arabic was added to 160 ml of boiling deionized water and mixed for 30 minutes. This was then added to the main phase and mixed for 1 hour. Third, sodium benzoate and citric acid were added directly to the main phase and mixed therewith for 15 minutes. Fourth, the Polysorbate 80 was dissolved in 10 ml of warm (55° C.) deionized water and then added to the main phase. The mixing container was rinsed with 10 ml of deionized water and the rinse was added to the main phase. The main phase was then mixed for 15 minutes. Fifth, the ibuprofen was added to the main phase and mixed for three hours. Next the colors and flavors were added as described in Example 1. The sucrose syrup #2 was added and the main phase mixed for an additional 30 minutes. The volume was then adjusted to 1 liter with deionized water, passed through a mill and then deaerated. The resulting material separated within one week and was deemed to be unacceptable. This demonstrates that not all water soluble suspending agents are useful as the first suspending agent in accordance with the present invention.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

I claim:

1. A storage stable aqueous suspension for delivery of at least one substantially water-insoluble pharmaceutically active agent comprising: at least one substantially water-insoluble pharmaceutically active agent provided in an amount which is effective to treat a patient in need of such treatment, said substantially water-insoluble pharmaceutically active agent being suspended in a formulation including a first suspending agent which is a pharmaceutically acceptable, non-ionic, water-soluble, modified cellulose, a second suspending agent which is water-soluble, hydrocolloidal polysaccharide, and a non-ionic, water-soluble wetting-agent, said first suspending agent, said second suspending agent and said wetting-agent be provided in amounts which are effective to form a stable suspension of said pharmaceutically active agent.

2. The suspension of claim 1 wherein, said substantially water-insoluble pharmaceutically active agent is selected from a group consisting of cardiovascular drugs, hypoglycemic drugs, sedatives/hypnotics; antiepileptics, psycholpharmacologic agents, analgesics, antipyretics, anti-inflammatory agents, anti-neoplastics, and antimicrobials, antihistamines and decongestants.

3. The suspension of claim 2 wherein said substantially water-insoluble pharmaceutically active agent be selected from a consisting of antihistamines, decongestants, antimicrobials, analgesic antipyretics and anti-inflammatory agents.

4. The suspension of claim 3 wherein said substantially water-insoluble pharmaceutically active agent is selected from a group consisting of an analgesic, antipyretic, and anti-inflammatory agents.

5. The suspension of claim 4 wherein said substantially water-insoluble pharmaceutically active agent is ibuprofen.

6. The suspension of claim 1 wherein said substantially water-insoluble pharmaceutically active agent is provided in an amount of between about 0.1% and about 20% w/v.

7. The suspension of claim 6 wherein said substantially water-insoluble pharmaceutically active agent is provided in an amount of between about 0.5% and about 10% w/v.

8. The suspension of claim 7 wherein said substantially water-insoluble pharmaceutically active agent is provided in an amount of between about 1.0% and about 4.0% w/v.

9. The suspension of claim 8 wherein said substantially water-insoluble pharmaceutically active agent is provided in an amount of about 2% w/v.

10. The suspension of claim 5 wherein said water-insoluble pharmaceutically active agent is provided in the amount of between about 0.5% and about 8% w/v.

11. The suspension of claim 1 wherein said modified cellulose is selected from the group consisting of hydroxypropylcellulose, methylcellulose, hydroxypropyl methylcellulose, and hydroxyethylcellulose.

12. The suspension of claim 11 wherein said modified cellulose is hydroxypropyl methylcellulose.

13. The suspension of claim 1 wherein said first suspending agent is provided in amounts of between about 0.4% and about 1.0% w/v.

14. The suspension of claim 13 wherein said first suspending agent was provided in an amount of between about 0.5% and about 0.7% w/v.

15. The suspension of claim 14 wherein said first suspending agent was provided as provided in an amount of about 0.6% w/v.

16. The suspension of claim 12 wherein said hydroxypropyl methylcellulose is provided in an amount of between about 0.4% and about 1.0% w/v.

17. The suspension of claim 1 wherein said second suspending agent is selected and provided in an mount such that it exhibits a shear thinning profile whereby for each log decrease of the shear rate in the range of 20 $sec^{-1}$ to 0.2 $sec^{-1}$, the viscosity of the suspension will increase at least 100%.

18. The suspension of claim 17 wherein said second suspending agent is selected from a group consisting of xanthan gum, guar gum, carrageenan gum, and gum arabic.

19. The suspension of claim 18 wherein said second suspending agent is xanthan gum.

20. The suspension of claim 1 wherein said second suspending agent is provided in an amount of between about 0.1% and about 1.0% w/v.

21. The suspension of claim 20 wherein said second suspending agent is provided in an amount of between about 0.1% and about 0.3% w/v.

22. The suspension of claim 21 wherein said second suspending agent is provided in an amount of about 0.15% and about 0.21% w/v.

23. The suspension of claim 19 wherein said xanthan gum is provided in the amount of between about 0.1% and about 0.3% w/v.

24. The suspension of claim 1 wherein said wetting agent is selected from the group consisting of polyoxyethylene sorbiton fatty acids esthers, poloxamers and polyvinyl alcohols.

25. The suspension of claim 1 wherein said wetting-agent is provided in an amount between about 0.025% and about 0.4% w/v.

26. The suspension of claim 25 wherein said wetting-agent is provided in an amount of between about 0.05% and about 0.2% w/v.

27. The suspension of claim 26 wherein said wetting-agent is provided in an amount of about 0.1% w/v.

28. The suspension of claim 24 wherein said wetting-agent is polyoxyethylene sorbitan monooleate provided in an amount of between about 0.025% and about 0.4% w/v.

29. The suspension of claims 1 or 11 comprising at least one additional material selected from a group consisting of a sweetener, a humectant, a viscosity modifier, an antimicrobial agent, a pH modifier, a flavoring and a coloring.

30. The suspension of claim 29 wherein said sweetener is selected from the group consisting of fructose, glucose, sorbitol, mannitol, xylitol and sucrose.

31. The suspension of claim 30 wherein said sweetener is provided in the amount of between about 20% and about 40% w/v.

32. The suspension of claim 31 wherein said sweetener is provided in the amount of between about 25% and about 35% w/v.

33. The suspension of claim 29 wherein said humectant is selected from a group consisting of sorbitol, propylene glycol and glycerin.

34. The suspension of claim 33 wherein said humectant is provided in an amount of between about 1% and about 40% w/v.

35. The suspension of claim 34 wherein said humectant is provided in an amount of between about 1% and about 15% w/v.

36. The suspension of claim 35 wherein said humectant is glycerin.

37. The suspension of claim 29 wherein said antimicrobial agent is selected from a group consisting of: potassium sorbate, sodium proprionate and sodium benzoate.

38. The suspension of claim 37 wherein said antimicrobial agent is provided in an amount of between about 0.05% and about 0.5% w/v.

39. The suspension of claim 38 wherein said is provided in an amount of between about 0.05% and about 0.5% w/v.

40. The suspension of claim 37 wherein said antimicrobial agent is sodium benzoate.

41. The suspension of claim 29 wherein said pH modifier is a pharmaceutically acceptable compound capable of establishing a pH for the suspension of between about 2.5 and about 5.0.

42. The suspension of claim 41 wherein said pH modifier is a pharmaceutically acceptable compound capable of establishing a pH for the suspension of between about 3.6 and about 4.6.

43. The suspension of claim 29 wherein said pH modifier is provided in an amount of between about 0.05% and about 1% w/v.

44. The suspension of claim 43 wherein said pH modifier is citric acid.

45. A storage stable, aqueous suspension for delivery of at least one substantially water-insoluble pharmaceutically active agent comprising: at least one substantially water-insoluble pharmaceutically active agent selected from a group consisting of: analgesics, antipyretics, and anti-inflammatory agent, said substantially water-insoluble pharmaceutically active agent being present in an amount of between about 0.1% and about 20% w/v; said pharmaceutically active agent being suspended in a formulation including a first suspending agent which is a pharmaceutically acceptable, non-ionic, water-soluble, modified cellulose provided in an amount of between about 0.4% and about 1% w/v, a second suspending agent which is a water-soluble, hydrocolloidal polysaccharide said second suspending agent be provided in amount of between about 0.1% and about 1.0% w/v and a water-soluble, non-ionic, wetting-agent provided in an amount of between about 0.025% and about 0.4% w/v.

46. The suspension of claim 45 wherein said substantially water-insoluble pharmaceutically active agent is provided in an amount of between about 0.5% and about 8% w/v, said first suspending agent is provided in an amount of between about 0.5% and about 0.7% w/v, said second suspending agent is provided in an amount of between about 0.15% and about 0.3% w/v and said wetting-agent provided in an amount of between about 0.05% and about 0.2% w/v.

47. The suspension of claim 46 wherein said substantially water-insoluble pharmaceutically active agent is ibuprofen, said first suspending agent is hydroxypropyl methylcellulose, said second suspending agent is xanthan gum and said wetting-agent is polyoxyethylene sorbitan monooleate.

48. The suspension of claim 47 wherein said ibuprofen is provided in amounts of about 2% w/v, said hydroxypropyl methylcellulose is provided in amount of about 0.6% w/v, said xanthan gum is provided in an amount of about 0.18% w/v and said polyoxyethylene sorbitan monooleate is provided in an amount of about 0.1% w/v.

49. The suspension of any of claims 45 through 48 further comprising a sweetener, at least one humectant or viscosity modifier, and an antimicrobial agent.

50. The suspension of claim 49 wherein said sweetener is sucrose provided in the amount of between about 25% and about 35% w/v, said humectant is glycerin provided in amount of between about 1% and about 15% w/v and said antimicrobial agent is sodium provided in an amount of between about 0.05% and about 0.5% w/v.

51. The composition of claim 50 further comprising a pH modifier provided in an amount which is effective to adjust the pH of the suspension of between about 2.5 and about 5.0.

52. A stabilized suspension comprising ibuprofen in amounts between about 0.5% and about 8% w/v, hydroxypropyl methylcellulose in an amount of between about 0.4% and about 1% w/v, xanthan gum provided in an amount of between about 0.1% and about 1.0% w/v, polyoxyethylene sorbitan monooleate in an amount of between about 0.025% and about 0.4% w/v, sucrose in an amount of between about 25% and about 35% w/v, glycerin in an amount of between about 1% and about 15% w/v, a antimicrobial agent in an amount of between about 0.05% and about 0.5% w/v; a pH modifier in an amount of between about 0.05% and about 0.5% w/v, at least one flavoring and water.

53. The suspension of claim 52 wherein said ibuprofen is provided in an amount of between about 1% and about 4% w/v, said hydroxypropyl methylcellulose is provided in an amount of between about 0.5% and about 0.7% w/v, said polyoxyethylene sorbitan monooleate is provided in an amount of between about 0.05% and about 0.2% w/v, and said xanthan gum is provided in an amount of between about 0.15% and about 0.2% w/v.

54. The suspension of claim 53 wherein said ibuprofen is provided in an amount of about 2% w/v, said hydroxypropyl methylcellulose is provided in an amount of about 0.6% w/v, said polyoxyethylene sorbitan monooleate is provided in an amount of about 0.1% w/v and said xanthan gum is provided in an amount of about 0.18% w/v.

55. A suspension for the administration of a substantially water-insoluble drug comprising: at least one substantially water-insoluble pharmaceutically active agent selected from a group consisting of: analgesics, antipyretics, and anti-inflammatory agent, said substantially water-insoluble pharmaceutically active agent being present in an amount of between about 0.1% and about 20% w/v; said pharmaceutically active agent being suspended in a formulation including a first suspending agent which is a pharmaceutically acceptable, non-ionic, water-soluble, modified cellulose provided in an amount of between about 0.4% and about 1% w/v, a second suspending agent exhibiting a shear thinning profile which is similar to the shear thinning profile of xanthan gum, said second suspending agent be provided in mount of between about 0.1% and about 1.0% w/v and a water-soluble, non-ionic, wetting-agent provided in an amount of between about 0.025% and about 0.4% w/v, said suspension containing no other significant amount of a generally water-insoluble composition of matter.

56. A suspension for the administration of a substantially water-insoluble drug consisting essentially of: at least one substantially water-insoluble pharmaceutically active agent selected from a group consisting of: analgesics, antipyretics, and anti-inflammatory agent, said substantially water-insoluble pharmaceutically active agent being present in an amount of between about 0.1% and about 20% w/v; said pharmaceutically active agent being suspended in a formulation including a first suspending agent which is a pharmaceutically acceptable, non-ionic, water-soluble, modified cellulose provided in an amount of between about 0.4% and about 1% w/v, a second suspending agent selected and provided in an amount such that it exhibits a shear thinning profile whereby for each log decrease of the shear rate in the range of 20 sec$^{-1}$ to 0.2 sec$^{-1}$, the viscosity of the suspension will increase at least 100%, a water-soluble, non-ionic, wetting-agent provided in an amount of between about 0.025% and about 0.4% w/v and water.

* * * * *

UNITED STATES PATENT AND TRADEMARK OFFICE
CERTIFICATE OF CORRECTION

PATENT NO. : 5,712,310
DATED : January 27, 1998
INVENTOR(S) : Koch

It is certified that error appears in the above-identified patent and that said Letters Patent is hereby corrected as shown below:

Column 1, line 24, "Drag" should read --Drug--.

Column 2, line 12, "drag" should read --drug--.

Column 3, line 18, "mount" should read --amount--.

Column 3, lines 24, 25, "provided in amount" should read --provided in an amount--.

Column 3, line 41, "inventions" should read --invention--.

Column 3, line 55, "drags" should read --drugs--.

Column 5, line 4, "agent," should read --agents,--.

Column 5, line 31, "have an median" should read --have a median--.

Column 6, line 49, "HPMC is Available" should read
-- HPMC is available --.

Column 6, line 65, "compounds are well" should read --compounds is well--.

Column 9, line 46, "of a week acid" should read --of a weak acid--.

UNITED STATES PATENT AND TRADEMARK OFFICE
CERTIFICATE OF CORRECTION

PATENT NO. : 5,712,310
DATED : January 27, 1998
INVENTOR(S) : Koch

It is certified that error appears in the above-identified patent and that said Letters Patent is hereby corrected as shown below:

Column 11, line 5, "added the main" should read --added to the main --.

Column 12, line 33, "HEC was used in place" should read -- HEC in place--.

Column 12, line 45, "L) was used in place" should read -- L) in place--.

Column 12, line 50, "Deionized" should read --deionized--.

Column 13, line 26, "wetting-agent be" should read --wetting-agent to be--.

Column 13, line 39, "analgesic antipyretics" should read --analgesic and antipyretics--.

Column 14, line 8, "was provided as provided" should read -- was provided as--.

Column 14, line 13, "an mount such" should read --an amount such--.

Column 15, line 40, "polysaccharide said" should read -- polysaccharide, said--.

Column 15, line 41, "be provided" should read --to be provided--.

Column 15, line 61, "provided in amount" should read --provided in an amount--.

UNITED STATES PATENT AND TRADEMARK OFFICE
CERTIFICATE OF CORRECTION

PATENT NO. : 5,712,310
DATED : January 27, 1998
INVENTOR(S) : Koch

It is certified that error appears in the above-identified patent and that said Letters Patent is hereby corrected as shown below:

Column 16, lines 3 and 4, "provided in amount" should read --provided in an amount--.

Column 16, line 18, "w/v. a anti-" should read --w/v. an anti--.

Column 16, lines 50 and 51, "agent be provided in mount of" should read --agent provided in an amount of --.

Signed and Sealed this

Second Day of June, 1998

Attest:

BRUCE LEHMAN

*Attesting Officer*        *Commissioner of Patents and Trademarks*